US011969334B2

United States Patent
Fujii et al.

(10) Patent No.: US 11,969,334 B2
(45) Date of Patent: Apr. 30, 2024

(54) ARTIFICIAL BLOOD VESSEL

(71) Applicant: Kake Educational Institution, Okayama (JP)

(72) Inventors: Yasuhiro Fujii, Okayama (JP); Susumu Ozawa, Okayama (JP); Tatsuyuki Nakatani, Okayama (JP); Yuichi Imai, Yokohama (JP)

(73) Assignee: KAKE EDUCATIONAL INSTITUTION, Okayama (JP)

( * ) Notice: Subject to any disclaimer, the term of this patent is extended or adjusted under 35 U.S.C. 154(b) by 600 days.

(21) Appl. No.: 17/273,970

(22) PCT Filed: Sep. 5, 2019

(86) PCT No.: PCT/JP2019/034997
§ 371 (c)(1),
(2) Date: Mar. 5, 2021

(87) PCT Pub. No.: WO2020/050365
PCT Pub. Date: Mar. 12, 2020

(65) Prior Publication Data
US 2021/0353404 A1    Nov. 18, 2021

(30) Foreign Application Priority Data

Sep. 5, 2018   (JP) ................................ 2018-165849

(51) Int. Cl.
*A61F 2/06*      (2013.01)
*A61F 2/00*      (2006.01)
(Continued)

(52) U.S. Cl.
CPC .............. *A61F 2/06* (2013.01); *C23C 16/045* (2013.01); *C23C 16/26* (2013.01); *C23C 16/503* (2013.01);
(Continued)

(58) Field of Classification Search
CPC ....................................................... A61F 2/06
See application file for complete search history.

(56) References Cited

U.S. PATENT DOCUMENTS

| 4,321,711 A | * | 3/1982 | Mano | ...................... A61L 27/56 |
| | | | | 623/1.49 |
| 5,437,900 A | * | 8/1995 | Kuzowski | ............... B29C 59/14 |
| | | | | 428/36.1 |

(Continued)

FOREIGN PATENT DOCUMENTS

| JP | S60-135062 A | 7/1985 |
| JP | 2006-263144 A | 10/2006 |

(Continued)

OTHER PUBLICATIONS

International Searching Authority, International Search Report and Written Opinion for International Application No. PCT/JP2019/034997, dated Nov. 5, 2019, (12 pages), Japan Patent Office, Tokyo, Japan.

(Continued)

*Primary Examiner* — Matthew J Lawson
*Assistant Examiner* — Yasniary De La Caridad Morales
(74) *Attorney, Agent, or Firm* — Alston & Bird LLP

(57) ABSTRACT

An artificial blood vessel 10 comprises: an artificial blood vessel body 12; and a carbon material film 11 that covers the inner wall of the artificial blood vessel body 12. The inner wall which is covered by the carbon material film 11 is configured so that the water vapor adsorption isotherm shows desorption hysteresis.

9 Claims, 8 Drawing Sheets

(51) Int. Cl.
    *C23C 16/04*     (2006.01)
    *C23C 16/26*     (2006.01)
    *C23C 16/503*     (2006.01)

(52) U.S. Cl.
    CPC ............... *A61F 2002/0081* (2013.01); *A61F 2002/0086* (2013.01); *A61F 2240/001* (2013.01)

(56) References Cited

U.S. PATENT DOCUMENTS

| | | | | |
|---|---|---|---|---|
| 5,628,786 | A | * | 5/1997 | Banas ............... B32B 27/08 623/1.13 |
| 2007/0204445 | A1 | * | 9/2007 | Hood ............... B29C 45/14 623/1.33 |
| 2013/0282108 | A1 | * | 10/2013 | Houston ........... B29C 45/14622 623/1.22 |
| 2020/0002809 | A1 | | 1/2020 | Imai et al. |

FOREIGN PATENT DOCUMENTS

| JP | 2015-167822 A | 9/2015 |
|---|---|---|
| JP | 2018-145478 A | 9/2018 |

OTHER PUBLICATIONS

Nakatani, Tatsuyuki et al. "Novel DLC Coating Technique On An Inner-Wall Of Extended Polytetrafluoroethylene Vascular Grafts Using Methand Plasma Produced By AC HV Discharge," *Journal of Photopolymer Science and Technology*, vol. 31, No. 3, Jun. 25, 2018, pp. 373-377. ISSN: 0914-9244.

* cited by examiner

ARTIFICIAL BLOOD VESSEL

CROSS REFERENCE TO RELATED APPLICATIONS

This application is a national stage application, filed under 35 U. S.C. § 371, of International Application No. PCT/JP2019/034997, filed Sep. 5, 2019, which international application claims further priority to and the benefit of Japanese Application No. 2018-165849, filed Sep. 5, 2018; the contents of both of which as are hereby incorporated by reference in their entireties.

BACKGROUND

Technical Field

The present disclosure relates to artificial blood vessels and production methods therefor.

Description of Related Art

Among medical materials for which there has in recent years been an increasing demand are artificial blood vessels. A commonly used artificial blood vessel is made of polytetrafluoroethylene (PTFE) expanded and made porous, which is called ePTFE (expanded-polytetrafluoroethylene). ePTFE is a highly biocompatible material, but does not provide sufficient patency to small artificial blood vessels. In particular, the use of an ePTFE artificial blood vessel having a diameter of less than 6 mm has a significantly high risk of occlusion.

Some small artificial blood vessels are made of a human or animal-derived material, but have problems with their safety and stable supply. Therefore, there is a demand for a small artificial blood vessel that is made of a non-biological material and is less likely to cause occlusion.

In order to reduce the occlusion of an artificial blood vessel made of ePTFE, various attempts have been made to modify the inner wall of the artificial blood vessel. One of them is to provide a biocompatible resin layer on the inner wall of ePTFE (see, for example, Japanese Unexamined Patent Publication No. 2015-167822 and Japanese Unexamined Patent Publication No. 2006-263144).

BRIEF SUMMARY

However, such a resin layer is likely to come off from the inner wall of ePTFE, posing a problem when the artificial blood vessel is used for a long period of time. In addition, the resin layer forms minute irregularities on the inner wall of the artificial blood vessel, which allow immune cells such as macrophages to be adsorbed on the surface, leading to formation of a non-uniform thick inner membrane. Therefore, such an artificial blood vessel is conversely more likely to cause occlusion, which is a problem.

The present disclosure describes an artificial blood vessel in which minute irregularities are reduced on the inner wall, and immune cells are less likely to be adsorbed by the inner wall.

An artificial blood vessel according to an embodiment of the present disclosure includes an artificial blood vessel body, and a carbonaceous film covering an inner wall of the artificial blood vessel body. A water vapor adsorption isotherm of the inner wall covered by the carbonaceous film has desorption hysteresis.

In the embodiment of the artificial blood vessel, the inner wall covered by the carbonaceous film may have a minute arithmetic average roughness of 2.5 or less as determined by image analysis.

In the embodiment of the artificial blood vessel, the inner wall covered by the carbonaceous film may have an immune cell adsorption amount of 20 cells/mm or less.

A method for producing an artificial blood vessel according to an embodiment, includes placing a porous artificial blood vessel body in a chamber in which internal pressure is adjustable, and generating plasma inside the artificial blood vessel body with a raw material gas containing a hydrocarbon supplied, to cover an inner wall of the artificial blood vessel body with a carbonaceous film. The artificial blood vessel body is placed in the chamber with the artificial blood vessel body inserted in a non-conductive outer tube having an inner diameter greater than an outer diameter of the artificial blood vessel body. A discharge electrode is provided at one end of the outer tube, and the other end of the outer tube is open. An alternating-current bias is intermittently applied between the discharge electrode, and a counter electrode spaced apart from the outer tube. A water vapor adsorption isotherm of the inner wall of the carbonaceous film has desorption hysteresis.

A device for producing an artificial blood vessel according to an embodiment, includes: a chamber in which internal pressure is adjustable; a gas supply unit configured to supply a hydrocarbon gas into the chamber; a discharge electrode and a counter electrode provided in the chamber; and a power supply unit configured to intermittently apply an alternating-current voltage between the discharge electrode and the counter electrode. The discharge electrode is attached to one end of an outer tube in which the artificial blood vessel body is inserted, and discharge is caused to occur with the counter electrode spaced apart from the outer tube so that plasma is generated in the outer tube, to form a carbonaceous film on an inner wall of the artificial blood vessel body. A water vapor adsorption isotherm of the inner wall covered by the carbonaceous film has desorption hysteresis.

The artificial blood vessel of the present disclosure is less likely to adsorb immune cells, and occlusion thereof can be prevented or reduced over a long period of time.

DETAILED DESCRIPTION OF VARIOUS EMBODIMENTS

Figure 1:
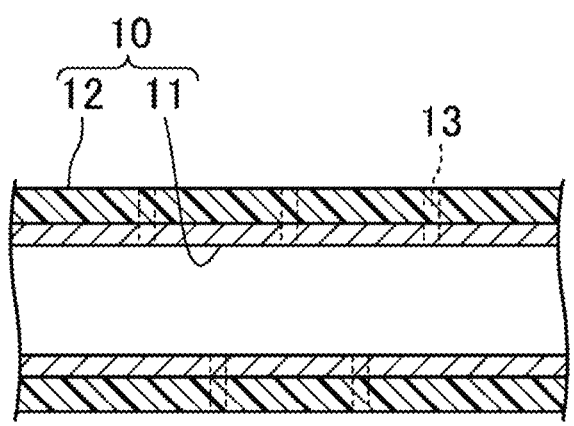
FIG. 1 is a cross-sectional view showing an artificial blood vessel according to one embodiment.

As shown in FIG. 1, an artificial blood vessel 10 according to an embodiment includes an artificial blood vessel body 12 that is made of porous expanded-polytetrafluoroethylene (ePTFE) and has pores 13, and a carbonaceous film 11 that covers the inner wall of the body 12.

As used herein, the carbonaceous film refers to a carbon-containing film, typified by hydrogenated amorphous carbon film and polymer-like carbon film, which are under standardization process by the International Organization for Standardization (ISO).

The inner wall of the artificial blood vessel body 12 made of ePTFE has minute irregularities, which serve as a scaffold that allows immune cells such as macrophages to be adsorbed by the inner wall of the artificial blood vessel. If a carbonaceous film having high surface smoothness is formed, the surface can be less likely to adsorb immune cells.

As used herein, immune cells mean white blood cells, including neutrophils, eosinophils, macrophages, lymphocytes, etc.

Specifically, the inner surface (the surface of the carbonaceous film 11) of the artificial blood vessel 10 covered by the carbonaceous film 11 preferably has a minute arithmetic average roughness (IARa) of 2.5 or less, more preferably 2.0 or less, and even more preferably 1.5 or less, as determined by image analysis. The inner surface of the artificial blood vessel 10 also preferably has a minute root mean square height (IARq) of 3.0 or less, more preferably 2.5 or less, and even more preferably 2.0 or less, as determined by image analysis. The inner surface of the artificial blood vessel 10 also preferably has a standardized arithmetic average roughness (SIARa) of 0.9 or less, more preferably 0.7 or less, and even more preferably 0.5 or less, and has preferably a standardized root mean square height (SIARq) of 0.8 or less, more preferably 0.7 or less, and even more preferably 0.5 or less, as standardized by the surface roughness of an untreated artificial blood vessel. The IARa and IARq can be measured by techniques described in examples below.

For the artificial blood vessel 10 covered by the carbonaceous film 11, it is preferable that desorption hysteresis should be observed in the water vapor adsorption isotherm thereof, and should not be observed in the nitrogen adsorption isotherm thereof. The water vapor adsorption isotherm and nitrogen adsorption isotherm can be measured by techniques described in examples below.

The inner surface of the artificial blood vessel 10 covered by the carbonaceous film 11 preferably has a water contact angle of 105° or less, more preferably 103° or less, and even more preferably 100° or less. The water contact angle as used herein can be measured by a technique described in examples below.

The artificial blood vessel 10 covered by the carbonaceous film 11 of this embodiment has an inner surface having improved smoothness and hydrophilicity compared to the artificial blood vessel body 12 not covered by the carbonaceous film 11, and therefore, allows a significant reduction in the adsorption amount of immune cells, and is less likely to cause occlusion. Specifically, the amount of immune cells that can be adsorbed by the inner surface of the artificial blood vessel 10 covered by the carbonaceous film 11 (also referred to as an "immune cell adsorption amount") is preferably 20 cells/mm or less, more preferably 15 cells/mm or less, even more preferably 10 cells/mm or less, and still even more preferably 6 cells/mm or less. The immune cell adsorption amount can be measured by a technique described in examples below.

For the artificial blood vessel 10 of this embodiment, when the carbonaceous film is formed, variations in the carbonaceous film inside the artificial blood vessel can be reduced, and therefore, the abovementioned surface state can be maintained at any of opposite end portions and a middle portion of the artificial blood vessel 10. Specifically, assuming that the artificial blood vessel 10 having a length of 150 mm is divided into about 2-cm segments, all of the segments are substantially identical in terms of the IARa, IARq, and hydrophilicity of the inner surface, and the immune cell adsorption amount to the inner surface.

In FIG. 1, the pore 13 is shown as a through hole that penetrates through the artificial blood vessel body 12. The artificial blood vessel body 12 is not limited to such a structure. The artificial blood vessel body 12 may have a porous structure having pores in a network structure, and the inside of the pores 13 may also be covered by the carbonaceous film 11. The outer wall of the artificial blood vessel body 12 may also be covered by the carbonaceous film 11.

Figure 2:
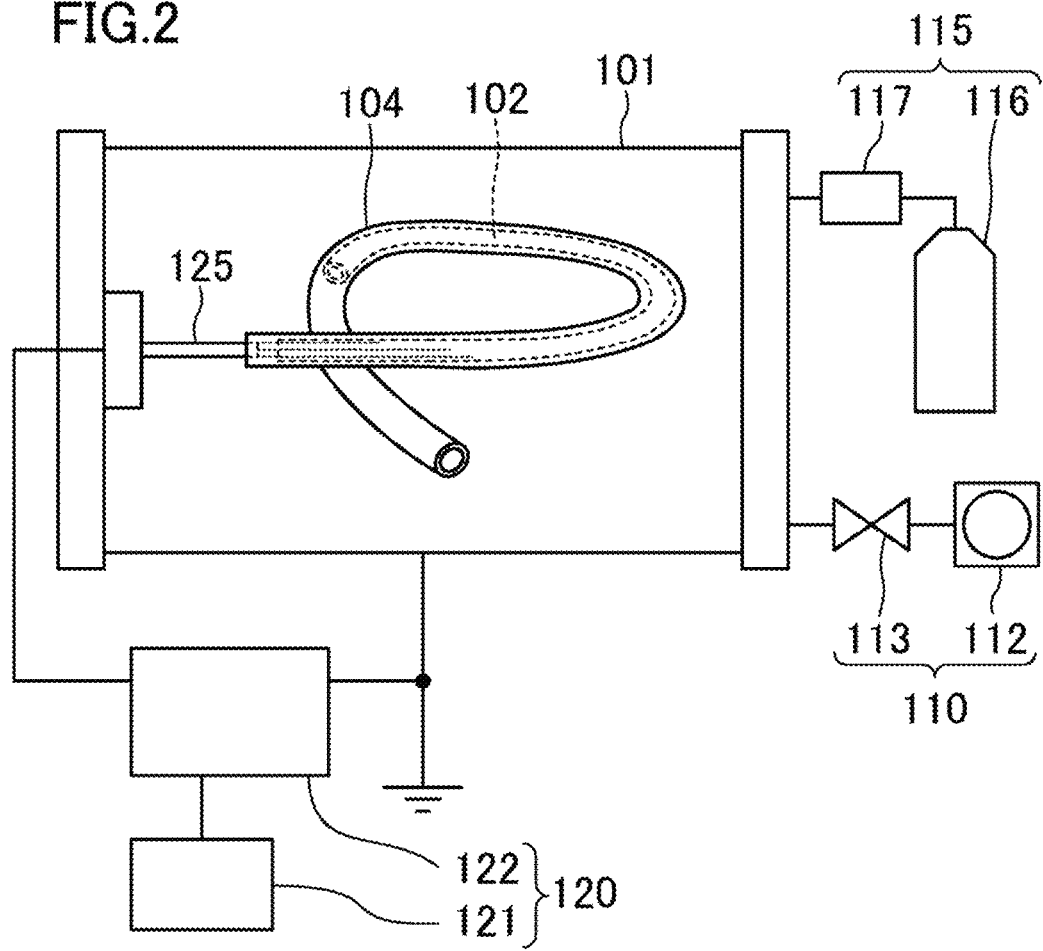
FIG. 2 is a schematic diagram showing a production device for an artificial blood vessel.

The inner wall of the artificial blood vessel body 12 can be covered by the carbonaceous film 11 in the following manner. FIG. 2 shows an example film-forming device for the carbonaceous film 11. The film-forming device has a chamber 101 that accommodates the artificial blood vessel body 12 in which a film is to be formed. The chamber 101 is coupled to a vacuum evacuation unit 110, and a gas supply unit 115 that supplies a film-forming gas into the chamber 101, and therefore, the internal pressure of the chamber 101 can be adjusted.

In this embodiment, the vacuum evacuation unit 110 has a vacuum pump 112 and a valve 113. In this embodiment, the gas supply unit 115 has a gas cylinder 116 and a mass flow controller 117. The gas supply unit 115 may be configured to supply a plurality of gases.

In this embodiment, a power supply unit 120 has a voltage generator 121 and an amplifier 122, and applies an alternating-current voltage between a discharge electrode 125 and a counter electrode. The counter electrode is a ground electrode, and forms the inner wall of the chamber 101.

In the chamber 101, the artificial blood vessel body 12 inserted in the outer tube 104 is placed. The outer tube 104 is non-conductive like the artificial blood vessel body 12 in order to allow generation of plasma therein. Specifically, the outer tube 104 is made of plastic or the like. The outer tube 104 can be formed of either a flexible soft material or a hard material. If the outer tube 104 is transparent or translucent, the generation of plasma can be advantageously visually observed.

An end of the outer tube 104 is positioned at the discharge electrode 125 with the other end thereof open. After the pressure in the chamber is reduced, a raw material gas containing a hydrocarbon is supplied from the gas supply unit 115, and an alternating-current voltage is applied between the discharge electrode 125 and the inner wall of the chamber 101, which serves as a counter electrode. By the application of an alternating-current voltage, temperature increases around the discharge electrode 125. As a result, the pressure inside the outer tube 104 is slightly lower than the pressure outside the outer tube 104, so that the plasma of the hydrocarbon is generated in the vicinity of the discharge electrode 125. As the other end of the outer tube 104 is open, the generated plasma moves to the open end of the outer tube 104, and therefore, plasma occurs throughout the outer tube 104. This allows formation of the carbonaceous film 11 on the inner wall surface of the artificial blood vessel body 12 inserted in the outer tube 104.

The inner diameter of the outer tube 104 is greater than the outer diameter of the artificial blood vessel body 12, and the outer tube 104 is long enough to accommodate the entire artificial blood vessel body 12. As the artificial blood vessel body 12 is inserted in the outer tube 104, whose wall surface does not have pores or the like, the carbonaceous film 11 can be formed on the inner wall of the porous artificial blood vessel body 12, which has pores in the wall surface, so that a pressure difference is less likely to occur between the inside and outside of the artificial blood vessel body 12.

If the inner diameter of the outer tube 104 is substantially equal to the outer diameter of the artificial blood vessel body 12, so that there is substantially no space between the outer wall surface of the artificial blood vessel body 12 and the inner wall surface of the outer tube 104, plasma is generated substantially only inside the artificial blood vessel body 12, and therefore, film formation can be performed only on the inner wall surface. If the space between the outer wall surface of the artificial blood vessel body 12 and the inner wall surface of the outer tube 104 is increased, plasma is also allowed to occur outside the artificial blood vessel body 12, whereby film formation can be performed on the outer wall surface as well as the inner wall surface of the artificial blood vessel body 12.

In order to sufficiently replace the gas in the chamber 101 with the raw material gas, the pressure in the chamber is preferably once reduced to about $1 \times 10^{-3}$ to $5 \times 10^{-3}$ Pa before film formation. The hydrocarbon contained in the raw material gas may be methane, ethane, propane, butane, ethylene, acetylene, benzene, etc., which are commonly used in CVD, and is preferably methane in terms of handling. Alternatively, the raw material gas may be a vaporized form of an organic silicon compound such as tetramethyl silane, or an oxygen-containing organic silicon compound such as hexamethyl disiloxane. The raw material gas may be optionally diluted with an inert gas, such as argon, neon, or helium, and then supplied, and is preferably argon in terms of handling. In the case of dilution, the ratio of the hydrocarbon and the inert gas is preferably about 10:1 to 10:5.

In order to form a uniform carbonaceous film on the inner wall of the artificial blood vessel body 12, the pressure in the chamber 101 is preferably about 5 to 200 Pa with the raw material gas supplied. The flow rate of the raw material gas may be about 50-200 sccm.

A bias voltage applied to the discharge electrode 125 during film formation may be about 1-20 kV. In order to avoid damage to the discharge electrode and temperature increase, the bias voltage is preferably 10 kV or less. The frequency of the alternating-current voltage is preferably from about 1-50 kHz. In order to reduce temperature increase, the alternating-current voltage is preferably a pulsed bias that is intermittently applied. In the case where the alternating current is in the form of burst waves, the pulse repetition frequency is preferably about 3-50 pps. The temperature of the tube can be adjusted to 200° C. or less by setting the pulse repetition frequency to about 30 pps or less, which depends on the inner diameter of the outer tube 104, the film formation time, the applied alternating-current voltage, etc. The pulse repetition frequency is increased in the case where a higher film formation rate is desired, and is decreased in the case where a reduction in temperature increase is desired.

In order to stabilize discharge and thereby achieve good adhesion of the carbonaceous film, a negative offset voltage is preferably applied to the discharge electrode 125. The offset voltage may be about 0-3 kV.

The material for the artificial blood vessel body 12 is not particularly limited, and may be porous ePTFE. Alternatively, the material for the artificial blood vessel body 12 may be polyester, other synthetic resins, etc.

The inner diameter of the artificial blood vessel body 12 is not particularly limited, and is preferably 10 mm or less, more preferably 6 mm or less, and even more preferably 4 mm or less, and preferably 0.1 mm or more, more preferably 0.2 mm or more. The length of the artificial blood vessel body 12 is not particularly limited, and in the case of an artificial blood vessel, catheter, etc., is preferably 2 cm or more, more preferably 4 cm or more, and even more preferably 10 cm or more. In order to form a uniform film, the length of the artificial blood vessel body 12 is preferably 5 m or less, more preferably 3 m or less, and even more preferably 1.5 m or less. Note that by adjusting the film formation conditions, a film can be formed on the inner wall of the artificial blood vessel body 12 having a length of 5 m or more.

Figure 3:
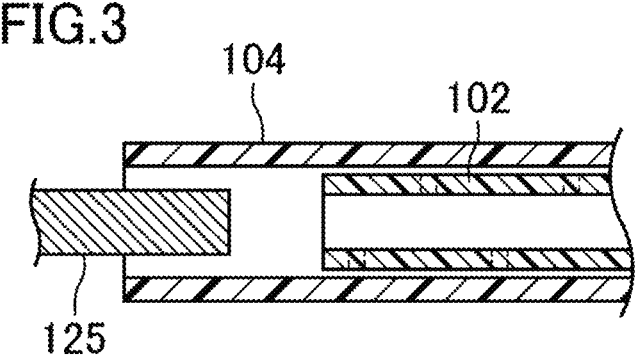
FIG. 3 is a cross-sectional view showing a portion where a discharge electrode is coupled.
Figure 4:
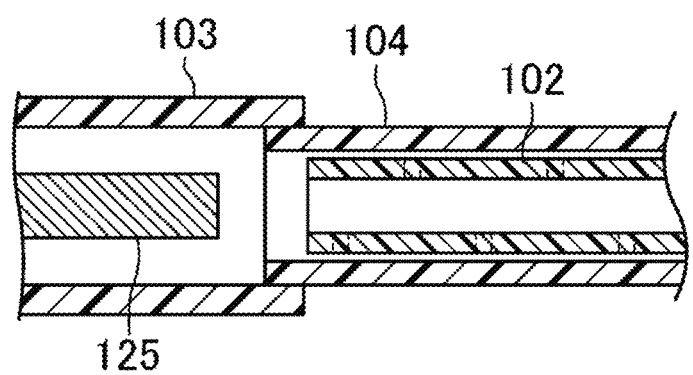
FIG. 4 is a cross-sectional view showing a variation of a portion where a discharge electrode is coupled.

The discharge electrode 125 is positioned at one end of the outer tube 104. In this embodiment, the discharge electrode 125 may be positioned at an end of the outer tube 104 in any of the following forms. Firstly, as shown in FIG. 3, at least a tip of the discharge electrode 125 may be positioned inside the outer tube 104. In this case, the tip of the discharge electrode 125 may be positioned inside the artificial blood vessel body 12. Alternatively, as shown in FIG. 4, an electrode connector 103 may be coupled to an end of the outer tube 104, and at least a tip of the discharge electrode 125 may be positioned inside the electrode connector 103. The electrode connector 103 may be formed of an insulating tube or the like. Although, in FIG. 4, the electrode connector 103 is a tube that is fitted on an outer surface of the outer tube 104, the electrode connector 103 may be a tube that is fitted into the outer tube 104. Alternatively, a plurality of tubes may be combined to form the electrode connector 103. In that case, a coupling portion to the outer tube 104 may be made of a hard material and the other portion may be made of a flexible material, which allows easy handling.

Figure 5:
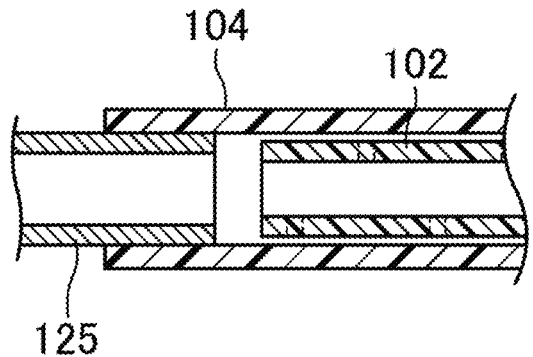
FIG. 5 is a cross-sectional view showing a variation of a portion where a discharge electrode is coupled.

If the outer diameter of the discharge electrode 125 is smaller than the inner diameter of the outer tube 104 or the electrode connector 103, the raw material gas can be supplied into the outer tube 104 from the end thereof closer to the discharge electrode 125. Alternatively, as shown in FIG. 5, the discharge electrode 125 may be hollow, through which the raw material gas can be supplied into the outer tube 104.

The discharge electrode 125 is conductive, and may be made of, for example, a metal. In the case where the discharge electrode 125 is made of a metal, the metal is preferably stainless steel in terms of corrosion resistance, etc. If a metal electrode is inserted in a small tube such that the metal electrode penetrates through the small tube, the metal is likely to be transferred from the electrode to the small tube. However, in the case of the film-forming device of this embodiment, if the electrode connector 103 is used, there is substantially no influence of the metal. Even in the case where the electrode connector 103 is not used, there is substantially no influence of the metal at a position about 5 cm or more away from the discharge electrode 125. In order to avoid the influence of the metal, the discharge electrode 125 is preferably a carbon electrode. In the film-forming device of this embodiment, a carbon electrode can also be easily formed.

Figure 6:
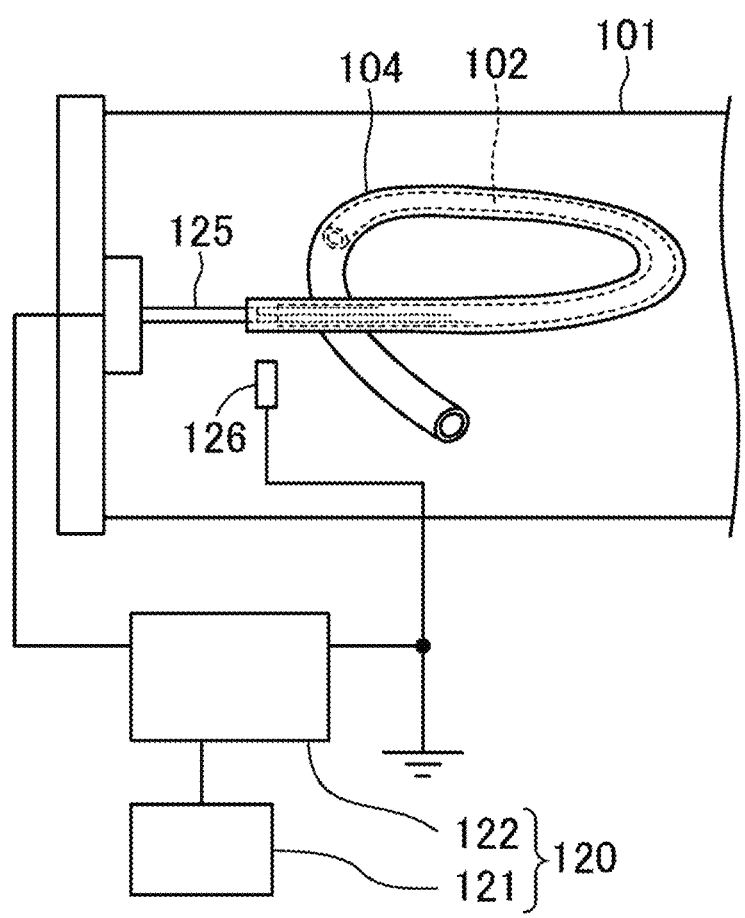
FIG. 6 is a cross-sectional view showing a variation of a counter electrode.

In this embodiment, the counter electrode is the inner wall of the chamber 101. Alternatively, as shown in FIG. 6, a counter electrode 126 may be positioned, facing the discharge electrode 125 with the outer tube 104 interposed therebetween. In the case where the counter electrode 126 is located at such a position, plasma can be stably generated even if the alternating-current voltage is reduced. The present disclosure is not limited to this. The counter electrode 126 may be located at any position in the chamber. Even if the counter electrode 126 is in contact with the outer tube 104, plasma can be generated. Note that the counter electrode 126 is preferably spaced apart from the outer tube 104 in terms of heat generation, etc.

The thickness of the carbonaceous film 11 formed on the inner wall of the artificial blood vessel body 12 is not particularly limited, and is preferably 3 nm or more, more preferably 10 nm or more, in order to improve the smoothness of the inner surface of the artificial blood vessel 100. The thickness of the carbonaceous film 11 is also preferably 50 nm or less, more preferably 30 nm or less, in order to prevent or reduce the coming off of the carbonaceous film 11, etc.

The film formation time is preferably 2 minutes or more, more preferably 3 minutes or more, in order to allow the inner wall surface of the artificial blood vessel body 12 to be completely covered by the carbonaceous film 11, which depends on the inner diameter of the long and small tube, the alternating-current voltage, the pulse repetition frequency, etc. The film formation time is also preferably 60 minutes or less, more preferably 30 minutes or less, and even more preferably 10 minutes or less, in terms of productivity.

EXAMPLES

<Device>

A carbonaceous film was formed on the inner wall surface of a sample using the film-forming device of FIG. 2. The chamber 101 was a stainless container having a diameter of 200 mm and a length of 500 mm. The chamber 101 was coupled to the vacuum evacuation unit 110 and the gas supply unit 115. The power supply unit 120 was provided with the voltage generator 121 (SG-4104, manufactured by Iwatsu Electric Co., Ltd.) and the amplifier 122 (HVA4321, manufactured by NF Corporation). The discharge electrode 125 was a stainless electrode having a diameter of 6 mm and a length of 70 mm. The gas supply unit 115 is configured to supply a raw material gas from the gas cylinder 116 of methane gas through the mass flow controller 117. The pressure in the chamber 101 was adjusted by controlling the opening degree of the valve and the amount of the gas supplied.

<Film Formation on Artificial Blood Vessel>

An ePTFE artificial blood vessel having an inner diameter of 3 mm, a thickness of 0.35 mm, and a length of 150 mm (SGTW-0315BT, manufactured by W. L. Gore & Associates, Inc.) was inserted in an outer tube that is a silicone tube having an inner diameter of 4 mm and a length of 150 mm, and thereafter, film formation was performed for a predetermined period of time.

The raw material gas was $CH_4$, the flow rate was 96.2 ccm (room temperature), and the pressure in the chamber was 39.06 Pa. During the film formation, the bias voltage was 5 kV, and the frequency was 10 kHz. The alternating-current voltage was intermittently applied for 5 minutes such that the pulse repetition frequency was 10 or 30 pps. Note that an offset of 2 kV was applied using the amplifier during the film formation.

<Measurement of Minute Surface Roughness>

The minute surface roughness was calculated by performing image processing on a photograph of the inner wall surface of the artificial blood vessel captured by a field emission scanning electron microscope (S-4800, manufactured by Hitachi High-Technologies Corporation). Initially, a 1290×960 portion of an electron microscopic photograph at 100K-fold magnification was captured as an image of 50×50 pixels into a computer. The value of the relative height of each pixel was calculated based on the luminances of the captured pixels, and was used as a pixel value. Next, noise was removed from the calculated pixel values by trend filtering (see Tibshirani, R.: Adaptive piecewise polynomial estimation via trend filtering, Annals of Statistics, 42(1), 285-323, 2014). Based on the pixel values after the noise removal, a minute arithmetic average roughness (IARa) was determined by image analysis using expression (1) below, and a minute root mean square height (IARq) was determined by image analysis using expression (2) below. Note that the calculations were performed for all of the 50×50 pixels, where n is 2500. Values obtained by dividing the resultant IARa and IARq values by the IARa and IARq values of an untreated artificial blood vessel are referred to as a standardized IARa and a standardized IARq, respectively.

$$MR_a = \frac{1}{n}\sum_{i=1}^{n} |P_i - \bar{P}| \qquad (1)$$

$$MR_q = \sqrt{\frac{1}{n}\sum_{i=1}^{n} (P_i - \bar{P})^2} \qquad (2)$$

<Measurement of Adsorption Isotherm>

The artificial blood vessel was cut into segments having a length of 10 mm, ten of which were then placed in a sample tube. For this sample, a water vapor adsorption/desorption isotherm and a nitrogen adsorption/desorption isotherm were obtained using a gas adsorption device (BELSORP 18, manufactured by MicrotracBEL Corporation). The sample was pretreated for degassing. The treatment temperature was 100° C. The treatment time was 3-8 hours. The treatment was ended after degassing was completed. For water vapor, the adsorption temperature was 25° C. In the pressure range of 0.4-2.9 kPa (relative pressure: 0.11-0.91), the adsorbed amount was measured at 20 points substantially equally spaced while the pressure was increased, and thereafter, the adsorbed amount was measured at 11 points while the pressure was decreased. For nitrogen, the adsorption temperature was −196° C. In the pressure range of 5.3-101 kPa (relative pressure: 0.05-1.0), the adsorbed amount was measured at 27 points substantially equally spaced while the pressure was increased, and thereafter, the adsorbed amount was measured at 14 points while the pressure was decreased.

<Measurement of Contact Angle>

The water contact angle of an ePTFE sheet surface having a thickness of 0.1 mm on which a carbonaceous film was formed was measured using a contact angle measurement device (DropMaster500, manufactured by Kyowa Interface Science Co., Ltd.). The amount of a water drop was 2 µL.

<Measurement of Immune Cell Adsorption Amount>

An artificial blood vessel was used to form an arterial-venous (A-V) shunt in each of left and right neck portions of a male goat weighing 35 kg under general anesthesia and heparin management. The artificial blood vessel was about 5 cm in length.

After the goat was kept in management of oral administration of aspirin for 8 weeks, the left and right artificial blood vessels were removed together with an artery and a vein under general anesthesia and heparin management. The removed blood vessel was washed with physiological saline, fixed with 10% formalin, paraffin-embedded, and cut into sections. The sections were prepared so as to show a transverse cross-section of the artificial blood vessel. The sections thus prepared were stained with hematoxylin-eosin (HE). The number of immune cells and the wall surface length (blood vessel length) of the artificial blood vessel were measured under a microscope to calculate the amount of immune cells adsorbed per millimeter of the blood vessel length. For seven sections, the amount of immune cells adsorbed per millimeter of the blood vessel length was measured, and the average value thereof was calculated. The magnification during observation was 100 times.

Example 1

Figure 7A:
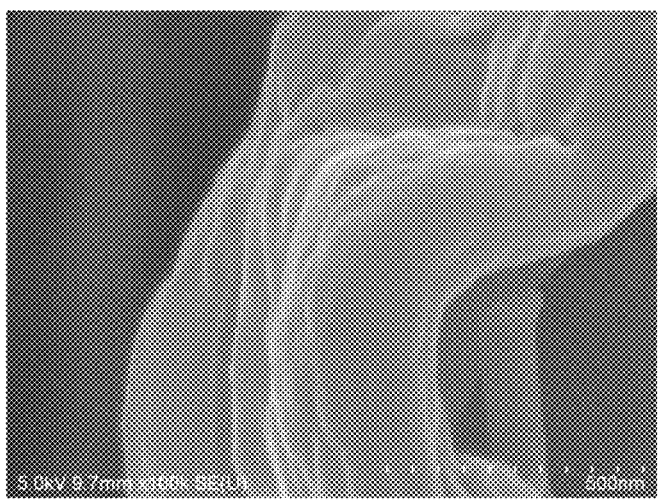
FIG. 7A is an electron microscopic photograph showing a surface of an artificial blood vessel in Example 1.
Figure 8A:
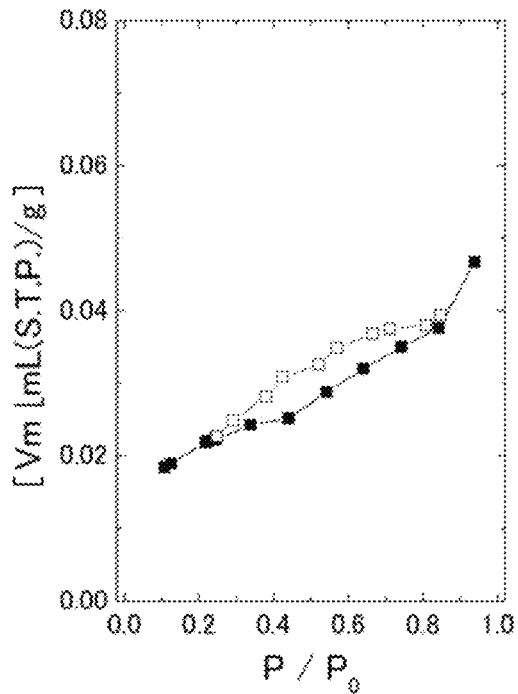
FIG. 8A is a water vapor adsorption isotherm of the artificial blood vessel in Example 1.
Figure 9A:
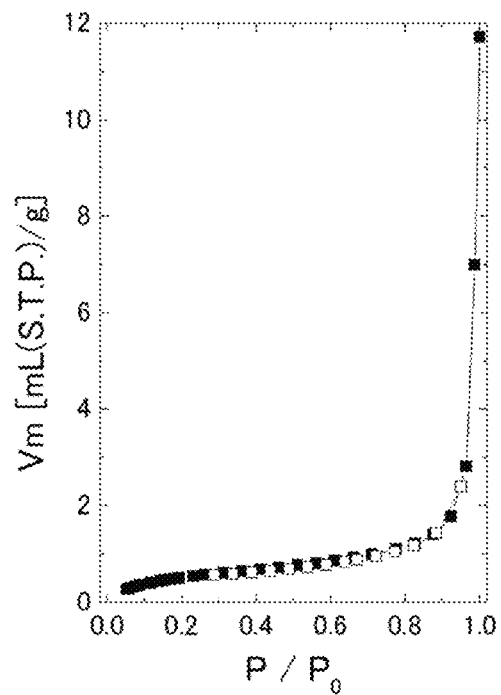
FIG. 9A is a nitrogen adsorption isotherm of the artificial blood vessel in Example 1.
Figure 10A:
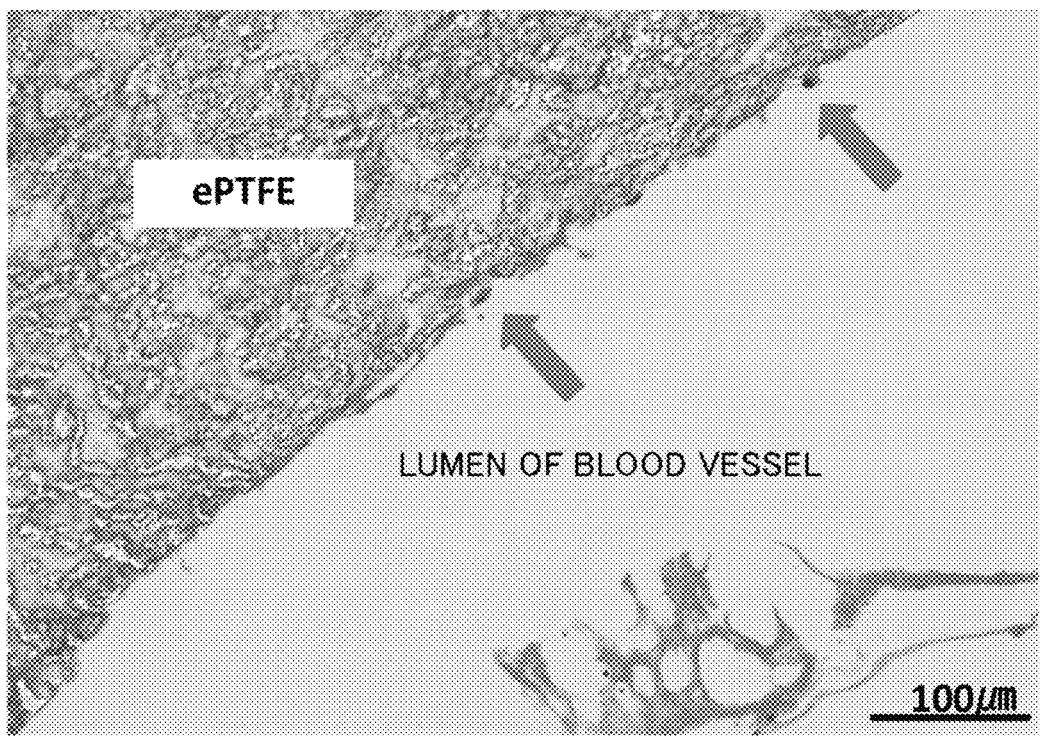
FIG. 10A is a microscopic photograph showing a state of the artificial blood vessel in Example 1 after being embedded.

A carbonaceous film was formed on the inner wall of an artificial blood vessel, where the film formation time was 5 minutes. A surface state of the resultant artificial blood vessel having the carbonaceous film is shown in FIG. 7A. In the SEM image shown in FIG. 7A, the IARa was 0.95, and the IARq was 1.2. The standardized IARa as standardized by the IARa of an untreated artificial blood vessel was 0.34, and the standardized IARq as standardized by the IARq of an untreated artificial blood vessel was 0.32. The water vapor adsorption isotherm had desorption hysteresis (FIG. 8A). Meanwhile, desorption hysteresis was not observed in the nitrogen adsorption isotherm (FIG. 9A). The water contact angle was 98°. The artificial blood vessel of this example was embedded in a left neck portion of a goat. As a result, as shown in FIG. 10A, few immune cells were adsorbed, i.e., the average value of the amount of immune cells adsorbed was 3 cells/mm.

Comparative Example 1

Figure 7B:
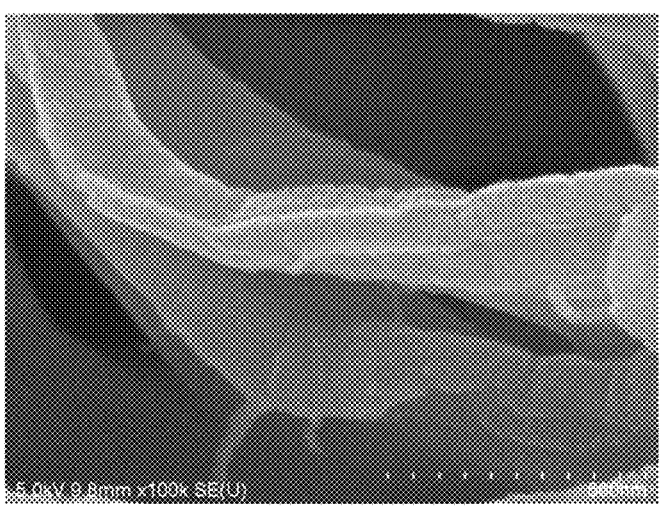
FIG. 7B is an electron microscopic photograph showing a surface of an artificial blood vessel in Comparative Example 1.
Figure 8B:
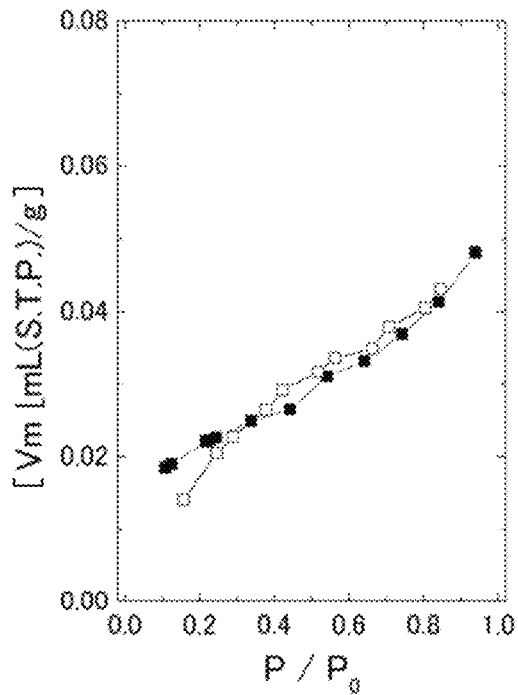
FIG. 8B is a water vapor adsorption isotherm of the artificial blood vessel in Comparative Example 1.
Figure 9B:
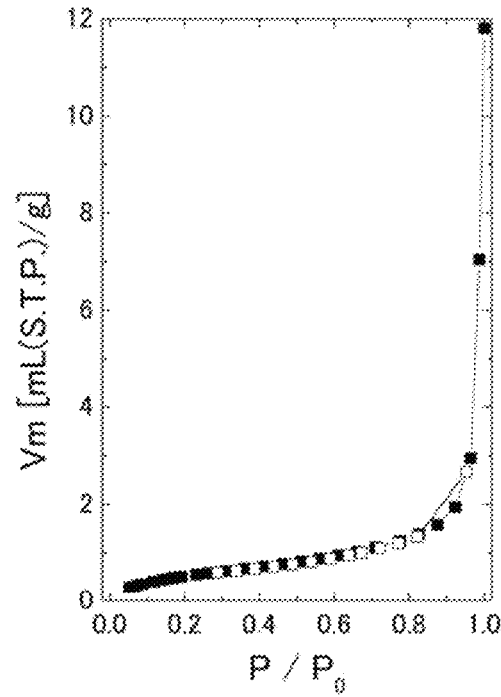
FIG. 9B is a nitrogen adsorption isotherm of the artificial blood vessel in Comparative Example 1.
Figure 10B:
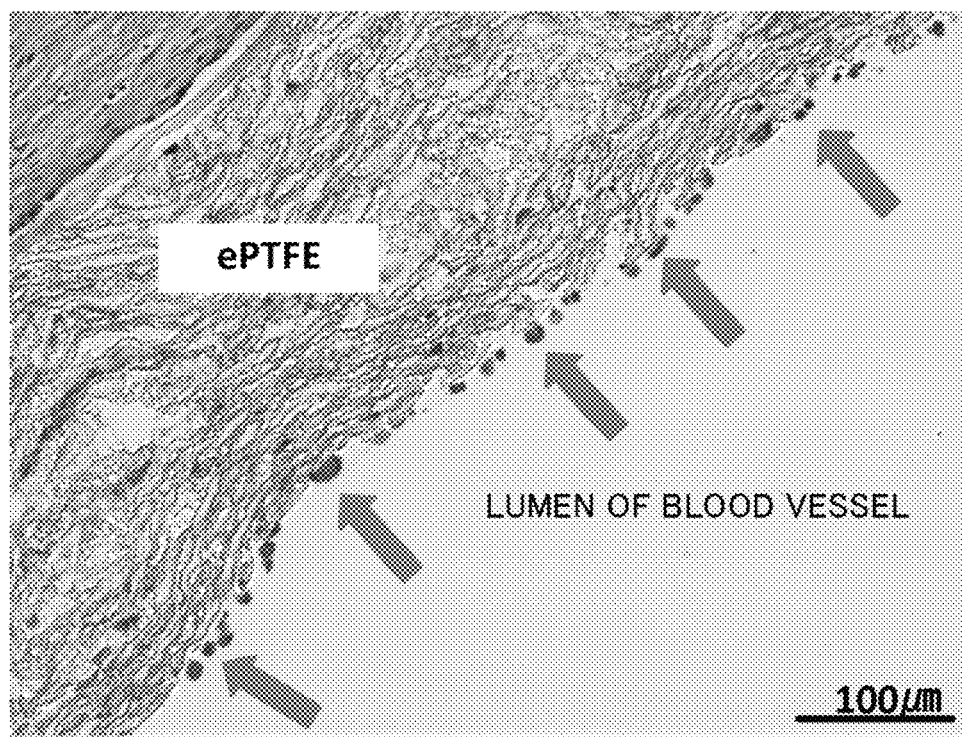
FIG. 10B is a microscopic photograph showing a state of the artificial blood vessel in Comparative Example 1 after being embedded.

A surface state of an artificial blood vessel in which a carbonaceous film was not formed is shown in FIG. 7B. In the SEM image shown in FIG. 7B, the IARa was 2.8, and the IARq was 3.6. Desorption hysteresis was not observed in the water vapor adsorption isotherm or in the nitrogen adsorption isotherm (FIGS. 8B and 9B). The water contact angle was 132°. The artificial blood vessel of this comparative example was embedded in a right neck portion of a goat. As a result, as shown in FIG. 10B, a large number of immune cells were adsorbed by the inner wall surface of the artificial blood vessel. The average value of the amount of immune cells adsorbed was 29 cells/mm.

Comparative Example 2

Figure 7C:
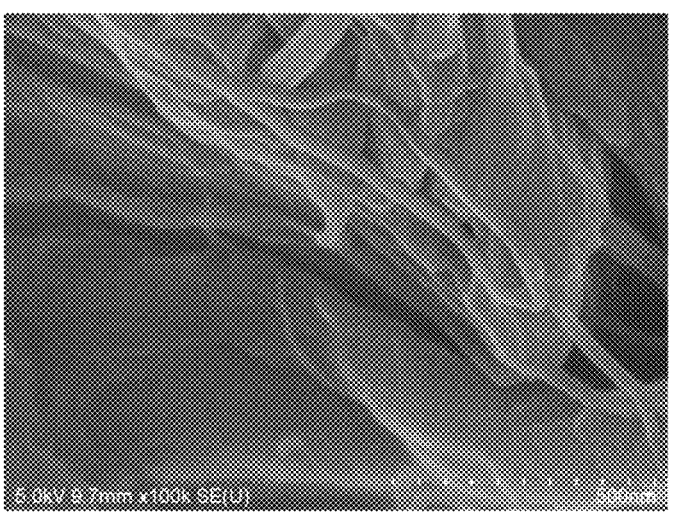
FIG. 7C is an electron microscopic photograph showing a surface of an artificial blood vessel in Comparative Example 2.

A carbonaceous film was formed in a manner similar to that of Example 1, except that the film formation time was 1 minute. A surface state of the resultant artificial blood vessel in which the carbonaceous film was formed is shown in FIG. 7C. Desorption hysteresis was not observed in the water vapor adsorption isotherm or in the nitrogen adsorption isotherm. The water contact angle was 107°.

Given the desorption hysteresis of the water vapor adsorption isotherm and the value of the water contact angle, the artificial blood vessel of Example 1 in which a carbonaceous film was formed is more hydrophilic than an untreated artificial blood vessel and the artificial blood vessel of Comparative Example 2. In addition, the surface smoothness was improved, and therefore, the immune cell adsorption amount was significantly reduced.

Conclusion

The artificial blood vessel of the present disclosure has few minute irregularities on the inner wall thereof, and therefore, immune cells are less likely to be adsorbed by the inner wall thereof. Therefore, the artificial blood vessel of the present disclosure is useful as a medical artificial blood vessel.

The invention claimed is:

1. An artificial blood vessel comprising:
   an artificial blood vessel body; and
   a carbonaceous film covering an inner wall of the artificial blood vessel body,
   wherein a water vapor adsorption isotherm of the inner wall covered by the carbonaceous film has desorption hysteresis.

2. The artificial blood vessel of claim 1, wherein the inner wall covered by the carbonaceous film has a minute arithmetic average roughness of 2.5 or less as determined by image analysis.

3. The artificial blood vessel of claim 2, wherein the inner wall covered by the carbonaceous film has substantially the same minute arithmetic average roughness at opposite end portions and a middle portion of the artificial blood vessel body.

4. The artificial blood vessel of claim 2, wherein:
   the inner wall covered by the carbonaceous film has a standardized arithmetic average roughness of 0.9 or less, and
   the standardized arithmetic average roughness is obtained by standardizing the minute arithmetic average roughness of the inner wall covered by the carbonaceous film based on the minute arithmetic average roughness of the inner wall not covered by the carbonaceous film.

5. The artificial blood vessel of claim 1, wherein the inner wall covered by the carbonaceous film has a water contact angle of 105° or less.

6. The artificial blood vessel of claim 1, wherein the inner wall covered by the carbonaceous film has an immune cell adsorption amount of 20 cells/mm or less.

7. The artificial blood vessel of claim 1, wherein:
   the artificial blood vessel body has pores in a network structure, and
   the carbonaceous film covers an inside of the pores.

8. A method for producing an artificial blood vessel, comprising:
   placing a porous artificial blood vessel body in a chamber in which internal pressure is adjustable, and
   generating plasma inside the artificial blood vessel body with a raw material gas containing a hydrocarbon supplied, to cover an inner wall of the artificial blood vessel body with a carbonaceous film,
   wherein:
   the artificial blood vessel body is placed in the chamber with the artificial blood vessel body inserted in a non-conductive outer tube having an inner diameter greater than an outer diameter of the artificial blood vessel body,
   a discharge electrode is provided at one end of the outer tube, and the other end of the outer tube is open,
   an alternating-current bias is intermittently applied between the discharge electrode, and a counter electrode spaced apart from the outer tube, and
   a water vapor adsorption isotherm of the inner wall of the carbonaceous film has desorption hysteresis.

9. A device for producing an artificial blood vessel, comprising:
   a chamber in which internal pressure is adjustable;
   a gas supply unit configured to supply a hydrocarbon gas into the chamber;
   a discharge electrode and a counter electrode provided in the chamber; and
   a power supply unit configured to intermittently apply an alternating-current voltage between the discharge electrode and the counter electrode,
   wherein:
   the discharge electrode is attached to one end of an outer tube in which the artificial blood vessel body is inserted and discharge is caused to occur with the counter electrode spaced apart from the outer tube so that plasma is generated in the outer tube, to form a carbonaceous film on an inner wall of the artificial blood vessel body, and
   a water vapor adsorption isotherm of the inner wall covered by the carbonaceous film has desorption hysteresis.

\* \* \* \* \*